US010292973B2

(12) United States Patent
Weinstock et al.

(10) Patent No.: US 10,292,973 B2
(45) Date of Patent: May 21, 2019

(54) COVALENT IRREVERSIBLE INHIBITORS OF USP7 AS ANTI-CANCER AGENTS

(71) Applicant: PROGENRA, INC., Malvern, PA (US)

(72) Inventors: Joseph Weinstock, Wayne, PA (US); Jian Wu, Chester Springs, PA (US); Suresh Kumar Kizhakkethil-George, Downingtown, PA (US); Feng Wang, Devon, PA (US); Matthew P. Kodrasov, Cherry Hill, NJ (US); Saket Agarwal, Woburn, MA (US)

(73) Assignee: PROGENRA, Inc., Malvern, PA (US)

( * ) Notice: Subject to any disclaimer, the term of this patent is extended or adjusted under 35 U.S.C. 154(b) by 0 days.

(21) Appl. No.: 15/748,830

(22) PCT Filed: Jul. 28, 2016

(86) PCT No.: PCT/US2016/044434
§ 371 (c)(1),
(2) Date: Jan. 30, 2018

(87) PCT Pub. No.: WO2017/023684
PCT Pub. Date: Feb. 9, 2017

(65) Prior Publication Data
US 2018/0228789 A1 Aug. 16, 2018

Related U.S. Application Data

(60) Provisional application No. 62/199,561, filed on Jul. 31, 2015.

(51) Int. Cl.
| | | |
|---|---|---|
| *A61K 31/4436* | (2006.01) |
| *A61K 31/10* | (2006.01) |
| *A61K 31/16* | (2006.01) |
| *A61K 31/381* | (2006.01) |
| *A61P 35/00* | (2006.01) |
| *C07D 409/12* | (2006.01) |
| *C07D 409/14* | (2006.01) |

(52) U.S. Cl.
CPC .......... *A61K 31/4436* (2013.01); *A61P 35/00* (2018.01); *C07D 409/12* (2013.01); *C07D 409/14* (2013.01); *A61K 31/10* (2013.01); *A61K 31/16* (2013.01); *A61K 31/381* (2013.01)

(58) Field of Classification Search
CPC .......... A61K 31/4436; A61K 2300/00; A61K 31/10; A61K 31/16; A61K 31/381; A61P 35/00; C07D 409/12; C07D 409/14
See application file for complete search history.

(56) References Cited

U.S. PATENT DOCUMENTS

| 8,680,139 B2 * | 3/2014 | Cao ...................... C07D 409/12 |
| | | 514/430 |
| 9,717,717 B1 | 8/2017 | Weinstock et al. |
| 2004/0122016 A1 | 6/2004 | Cao et al. |
| 2007/0191420 A1 | 8/2007 | Leysen et al. |

OTHER PUBLICATIONS

Chauhan, et al., "A Small Molecule Inhibitor of Ubiquitin-Specific Protease-7 Induces Apoptosis in Multiple Myeloma Cells and Overcomes Bortezomib Resistance" Cancer Cell (2012) 22(3):1-26.
Bacchetta, et al., "From IPEX syndrome to FOXP3 mutation: a lession on immune dysregulation", Ann. N.Y. Acad. Sci. (2016) 1417(1):5-22.
American Cancer Society, "Cancer Facts and Figures: 2011" (2011) American Cancer Society, Atlanta, GA.
Felle, et al., "The USP7/Dnmt1 complex stimulates the DNA methylation activity of Dnmt1 and regulates the stability of UHRF1" Nucleic Acids Research (2011) 39(19):8355-8365.
Fridman, et al., "The immune contexture in human tumours: impact on clinical outcome", Nature (2012) 12:298-306.
D'Hennezel, et al., "FOXP3 forkhead domain mutation and regulatory T cells in the IPEX syndrome" N. Engl. J. Med. (2009) 361(17):1710-3.
Nicholson, et al., "The Multifaceted Roles of USP7: New Therapeutic Opportunities" Cell Biochem. Biophys. (2011) 60:61-68.
Obata, et al., "The epigenetic regulator Uhrf1 facilitates the proliferation and maturation of colonic regulatory T cells" Nature Immunology (2014) 15(6): 571-579 (2014).
Pardoll, D.M., "The blockade of immune checkpoints in cancer immunotherapy" Nature Reviews Cancer (2012) 12: 252-264.
Pedroza-Pacheco, et al., "Interaction between natural killer cells and regulatory T cells: perspectives for immunotherapy" Cellular & Molecular Immunology (2013) 10:222-229.
Qin, et al., "Usp7 and Uhrf1 control ubiquitination and stability of the maintenance DNA methyltransferase Dnmt1" J. Cell Biochem. (2011) 112(2):439-444.
Singh, et al., "The resurgence of covalent drugs" Nature Reviews Drug Discovery (2011) 10:307-316.
Van Loosdregt, et al., "Stabilization of the Transcription Factor Foxp3 by the Deubiquitinase USP7 Increases Treg-Cell-Suppressive Capacity" (2013) Immunity 39:259-271.
Wang, et al., "Foxp3+ T-regulatory cells require DNA methyltransferase 1 expression to prevent development of lethal autoimmunity" Blood (2013) 121(18): 3631-3639.
Wang, et al., "Regulatory T cells and B cells: implication on autoimmune diseases" Int. J.Clin. Exp. Pathol. (2013) 6:(12):2668-2674.
Weinstock, et al., "SelectiveDual Inhibitors of the Cancer-Related Deubiquitylating Proteases USP7 and USP47" ACD Med. Chem. Lett. (2012) 3(10):789-792.
Wolchok, et al., "Nivolumab plus Ipilimumab in Advanced Melanoma" N. Engl. J. Med. (2013) 369:122-133.

* cited by examiner

*Primary Examiner* — Erich A Leeser
(74) *Attorney, Agent, or Firm* — Robert C. Netter, Jr.; Dann, Dorfman, Herrell & Skillman

(57) ABSTRACT

Compounds and pharmaceutical compositions for treating cancer by, for example, modulating immune system activity, are provided.

27 Claims, 8 Drawing Sheets

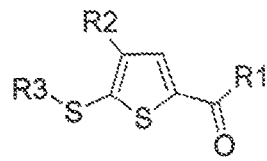

| Cpd | R1 | R2 | R3 | EC₅₀ (µM) for inhibition of | |
|---|---|---|---|---|---|
| | | | | USP7 | USP47 |
| 1 | 1-Methylpiperidin-4-NH | nitro | 3,5-Dichloro-pyridyl | 1.7 | 1.3 |
| 2 | 4-MeO-phenyl-NH | nitro | 3,5-Dichloro-pyridyl | 0.43 | 0.87 |
| 3 | 4-[2-(dimethylamino)ethoxy]-phenyl-NH | nitro | 3,5-Dichloro-pyridyl | 0.50 | 0.45 |
| 4 | 2-(Methylsulfonyl)-phenyl-NH | nitro | 3,5-Dichloro-pyridyl | 0.85 | 9.3 |
| 5 | 3-(Methylsulfonyl)-phenyl-NH | nitro | 3,5-Dichloro-pyridyl | 0.51 | 1.4 |
| 6 | 4-(Methylsulfonyl)-phenyl-NH | nitro | 3,5-Difluoro-pyridyl | 6.8 | 11.8 |
| 7 | 3-(Methylsulfamoyl-phenyl-NH | nitro | 3,5-Dichloro-pyridyl | 0.64 | 1.28 |
| 8 | 3-(Ethylsulfonyl)-phenyl-NH | nitro | 3,5-Dichloro-pyridyl | 0.42 | 0.94 |
| 9 | 3-(Cyclopropylsulfonyl)-phenyl-NH | nitro | 3,5-Dichloro-pyridyl | 0.56 | 1.59 |
| 10 | 3-(Cyclopropylmethylsulfonyl)-phenyl-NH | nitro | 3,5-Dichloro-pyridyl | 0.39 | 1.5 |

Fig. 3A

| Cpd | R | EC₅₀ (μM) for inhibition of | |
|---|---|---|---|
| | | USP7 | USP47 |
| 11 | 1,1-dioxidothiomorpholino | 4.3 | 6.4 |
| 12 | 1,1-dioxidotetrahydro-2H-thiopyran-4-yl-NH | 2.1 | 3.5 |
| 13 | 1,1-dioxidothiochroman-4-yl-NH | 0.81 | 1.6 |
| 14* | 4,4-dioxidohexahydropyrano[3,4-b][1,4]thiazin-1(5H)-yl-NH | 4.8 | 4.1 |

* Racemate

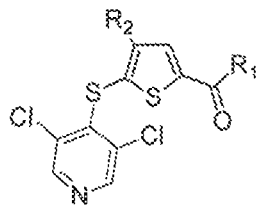

| Cpd | R1 | R2 | EC₅₀ (μM) for inhibition of | |
|---|---|---|---|---|
| | | | USP7 | USP47 |
| 15 | 1,1-dioxidobenzo(b)thien-6-yl-NH | nitro | 0.1 | 1.33 |
| 16 | 2,3-dihydro-1,1-dioxidobenzo(b)thien-6-yl-NH | nitro | 0.13 | 2.03 |
| 17 | 1,1-dioxidobenzo(b)thien-6-yl-NH | cyano | 0.59 | 5.1 |
| 18 | 3-methyl-1,1-dioxidobenzo(b)thien-6-yl-NH | nitro | 0.17 | 0.36 |
| 19* | 3-methyl-2,3-dihydro-1,1-dioxidobenzo(b)thien-6-yl-NH | nitro | 0.075 | 0.52 |
| 20* | 3-{[2-(dimethylamino)ethyl]amino}-2,3-dihydro-1,1-dioxidobenzo(b)thien-6-yl-NH | nitro | 0.22 | 0.20 |
| 21* | 3-[(2-methoxyethyl)amino]-2,3-dihydro-1,1-dioxidobenzo(b)thien-6-yl-NH | nitro | 0.79 | 2.0 |
| 22* | 3-[imino(methyl)oxo-sulfanyl]phenyl-NH | nitro | 2.0 | 2.2 |
| 23* | 1-imino-3-methyl-1-oxido-2,3-dihydro-1H-1-benzo[b]thiophen-6-yl-NH | nitro | 0.47 | 1.1 |

* Racemate

Fig. 3C

COVALENT IRREVERSIBLE INHIBITORS OF USP7 AS ANTI-CANCER AGENTS

CROSS-REFERENCE TO RELATED APPLICATIONS

The present application is a § 371 application of PCT/US2016/044434, filed Jul. 28, 2016, which claims the benefit of U.S. Provisional Patent Application No. 62/199,561, filed Jul. 31, 2015, the entire disclosures of which are incorporated by reference herein.

FIELD OF THE INVENTION

The present invention relates generally to pharmaceutical compositions for modulating cancer cell growth and immunological responses beneficial for the treatment of cancer, and more particularly, but not exclusively, to compositions of certain irreversible Ubiquitin Specific Protease 7 (USP7, also known as HAUSP) inhibitors capable of increasing the activity of Teff cells by reducing the activity of Treg cells.

BACKGROUND OF THE INVENTION

Cancer continues to have a huge social and economic impact. In 2011, 571,950 Americans died of cancer (~25% of all deaths), with US cancer-associated costs of $263.8 billion: $102.8 billion for direct medical costs (total health expenditures); $20.9 billion for indirect morbidity costs (lost productivity); and $140.1 billion for indirect mortality costs (lost productivity from premature death). Lung cancers (-14% small cell lung cancer, SCLC, ~85% non-small cell lung cancer, NSCLC) are the most common causes of cancer-related deaths in men and women; 156,940 patients died from lung cancer in 2011. The 5-yr survival for all stages combined is only 16%, regardless of progress in surgical management, radiation and chemotherapy [1]. Accordingly, there is a need in the field for compounds and methods for treating the numerous varieties of cancer.

In the development of new treatment modalities for cancer, there has been a resurgence of interest in drugs that form a covalent attachment to their target, especially with respect to drugs that are selective for their target [2].

The present invention includes a class of small molecule USP7 inhibitors, that have been identified to inhibit tumor growth by several mechanisms.

SUMMARY OF THE INVENTION

The present invention provides pharmaceutical compositions for treating cancers in patients in need thereof by inhibiting growth of tumor cells as well as by modulating immune system activity. For example, the advantages of the irreversible inhibitors of the invention include a long duration of action after only a short exposure to their target. If a drug has a short $t_{1/2}$ the possibility of off target toxicity is minimized [2]. Indeed, certain compounds of this invention, for example, exhibit such activity both in vitro and in vivo.

Inhibition of USP7 may inhibit tumor growth by modulating or promoting the activity of the immune system. Thus inhibition of USP7 can decrease or reduce the activity of regulatory T cells (Treg cells), which may increase the activity or number of killer effector T cells (Teff cells) in the tumor microenvironment. A decrease in Treg cell activity may include, for example, down regulation of Treg cells, and/or a reduction in the number of Treg cells present in a subject, and/or the general reduction in Treg cell function or activity as measured by an assay known to persons having ordinary skill in the art, which is indicative of Treg cell function. Conversely, an increase in Teff cell activity may include, for example, upregulation of Teff cells, and/or an increase in the number of Teff cells present in a subject, and/or the general increase in Teff cell function and/or activity as measured by an assay known to persons having ordinary skill in the art, which is indicative of Teff cell function.

U.S. Pat. No. 8,680,139, which is incorporated by reference herein [3], discloses certain thiophene compounds that inhibit the deubiquitination of enzyme USP7. USP7 has been linked genetically and/or biochemically with cancer including cancers of the prostate, lung, liver, brain, and also multiple myeloma. USP7 has been shown to deubiquitinate and stabilize several substrates that are pro-oncogenic and or involved in immunoevasion of cancers. Notable examples include HDM2, UHRF1, DNMT1, TIP60, Claspin, Chk1 and Foxp3 [4-6]. Many of these substrates as well as USP7 are highly expressed in a variety of cancers and their downregulation has been shown to result in inhibition of tumor growth. In particular, downregulation or disruption of HDM2, UHRF1, DNMT1, TIP60 and Chk1 have been shown to inhibit growth of cancer cells as well as sensitize them for chemo- and radiotherapies.

USP7 preferentially deubiquitinates HDM2, which increases its cellular concentration. This ligase causes ubiquitination of the tumor suppressor p53, which is a cancer suppressor which works by promoting cell cycle arrest and apoptosis of cancer cells. Thus USP7 inhibitors exhibited anti-cancer properties against a variety of tumor types by directly impacting the growth and or promoting apoptosis of tumors.

In one aspect, the invention provides compounds and pharmaceutical compositions for treating cancer in a patient in need of such treatment. The cancers treated by the compounds and pharmaceutical compositions of the invention may include lung, ovary, endometrium, cervix, breast, prostate, head and neck, esophagus and stomach, liver, bladder, brain, pancreas, colon, and skin cancer as well as leukemia and multiple myeloma. For example, the present invention includes compounds and pharmaceutical compositions for treating cancer in a patient in need thereof by modulating immune system activity. The pharmaceutical compositions may include an amount of a USP7 inhibitor (USP7i) that may be effective to reduce Treg cell activity and/or increase Teff cell activity. The USP7i may be at least one compound of formula I:

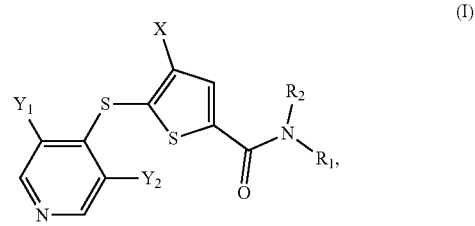

wherein X is nitro or cyano;

$Y_1$ and $Y_2$ may be the same or different and represent halogen, alkyl or haloalkyl;

$R_1$ may be selected from the group consisting of optionally substituted aryl, arylalkyl, heteroaryl, and heteroarylalkyl, and wherein said optionally substituted aryl, arylalkyl, heteroaryl, and heteroarylalkyl is substituted with one or more substituents selected from the group consisting of halo, hydroxyl, and optionally substituted alkyl, aryl, heteroaryl, cycloalkyl, heterocycle, alkoxy, hydroxyl, mercapto, aryloxy, heteroalkoxy, alkynyl, alkyl-S(O)$_n$, aryl-S(O)$_n$, sulfonamide, sulfamide, sulfoxy, sulfonyl, amido, alkyl-SO$_2$NR$_3$R$_4$, heteroalkyl-NR$_3$R$_4$, cyano, —C(O)OH, —C(O)OR$_3$, carboxamido, amino, monoalkylamino, dialkylamino, dialkylaminoalkylamino, NR$_3$R$_4$, alkylthio, acetamido, and C(O)NR$_3$R$_4$;

n may be 0-2;

R$_2$ may be hydrogen or optionally substituted alkyl;

or R$_1$ and R$_2$, together with the nitrogen atom to which they are attached form an optionally substituted heterocycle group.

R$_3$ and R$_4$ may be independently selected from the group consisting of H and optionally substituted alkyl, cycloalkyl, aryl, and heteroaryl, where R$_3$ and R$_4$ may be taken together to form an optionally substituted 3-, 4-, 5-, or 6-member carbocycle or heterocycle; and the pharmaceutically acceptable salts thereof.

Alternatively, R$_1$ may represent an optionally substituted 1,1 dioxidotetryadro-2H-thiopyran-4-yl group, which may be fused to an optionally substituted aryl, cycloalkyl, heteroaryl or heterocyclic group.

In one embodiment, R$_1$ and R$_2$, together with the nitrogen atom to which they are attached form an optionally substituted heterocycle group.

In other embodiments, the pharmaceutical compositions of the invention may include a USP7i that includes at least one compound of formula I, wherein R$_1$ may include a substituent selected from the group consisting of 4-(methylsulfonyl)-phenyl, 3-Chloro-4-(methylsulfonyl)-phenyl, 3-methoxy-4-(Methylsulfonyl)-phenyl, 3-(Methylsulfonyl)-phenyl, 3-(cyclopropylsulfonamido)-phenyl, 3-(cyclopropylmethylsulfonyl)-phenyl, 3-(Methylsulfonamido)-phenyl, 2-(Methylsulfonyl)-phenyl, 4-MeO-phenyl, 3-[2-(Me$_2$N)-ethoxy]phenyl, 4-[2-(Me$_2$N)-ethoxy]phenyl, 3-pyridinyl, 3-(ethylsulfonyl)-phenyl, 3-(isopropylsulfonyl)-phenyl, 3-(cyclopentylsulfonyl)-phenyl, 3-(methylthionyl)-phenyl, 3-(methylsulfonylmethyl)-phenyl, 3-(N-methylsulfonamido)-phenyl, 3-(trifluoromethylsulfonyl)-phenyl, 3-(2-ethoxysulfonyl)-phenyl, 1,1-dioxidobenzo(b)thien-6-yl, 3-methyl-1,1-dioxidobenzo(b)thien-6-yl, 2,3-dihydro-1,1-dioxidobenzo(b)thien-6-yl, 3-{[2-(dimethylamino)ethyl]amino}-2,3-dihydro-1,1-dioxidobenzo(b)thien-6-yl, 3-[2-(dimethylamino)ethoxy]-2,3-dihydro-1,1-dioxidobenzo(b)thien-6-yl, 1,1,3-trioxo-2,3-dihydro-2-benzothiazol-6-yl, 1H-indo-6-yl, 1H-1,3-benzodiazol-2-yl, 6-methanesulfonyl-1,3-benzothiazol-2-yl, Isoquinolin-5-yl, and 3-[imino(methyl)oxo-sulfanyl]phenyl.

In another embodiment, pharmaceutical compositions of the invention may include at least one USP7i of formula II:

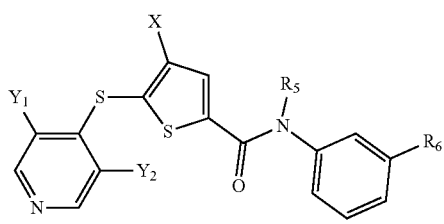

(II)

wherein X is nitro or cyano;
Y$_1$ and Y$_2$ may be the same or different and represent halogen, alkyl or haloalkyl;

R$_5$ may be H or optionally substituted alkyl; R$_6$ may be selected from the group consisting of H, halo, hydroxyl, and optionally substituted alkyl, aryl, alkoxy, aryloxy, heteroaryl, cycloalkyl, heteroarylalkyl, sulfonyl, sulfamide, sulfonamide, —C(O)OH, —C(O)OR$_7$, carboxamido, amino, monoalkylamino, dialkylamino, dialkylaminoalkylamino, thionyl, sulfoxy, alkyl-S(O)$_n$, and aryl-S(O)$_n$; R$_7$ may be H or alkyl; n may be 0-2; and the pharmaceutically acceptable salts thereof.

In an additional embodiment, the pharmaceutical compositions of the invention may include at least one USP7i of formula II, wherein R$_6$ may be a substituent selected from the group consisting of halo, methoxy, methylsulfonyl, ethylsulfonyl, propylsulfonyl, isopropylsulfonyl, cyclopropylsulfonyl, cyclobutylsulfonyl, cyclopentylsulfonyl, cyclohexylsulfonyl, methylthionyl, methylsulfoxyl, methylsulfonylmethyl, N-methylsulfonamido, trifluoromethylsulfonyl, 2-hydroxyethylsulfonyl, cyclopropylsulfonamido, cyclopropylmethylsulfonyl, methylsulfonamido, 2-(Me$_2$N)-ethoxy, and pyridinyl.

In further embodiments of the invention, the pharmaceutical compositions may include at least one USP7i of formula III:

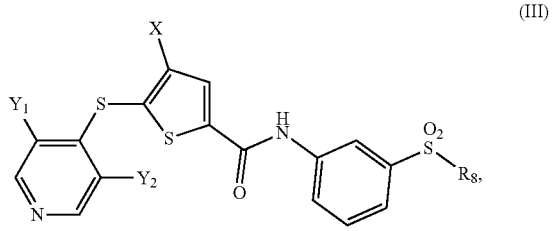

(III)

wherein X is nitro or cyano;
Y$_i$ and Y$_2$ may be the same or different and represent halogen, alkyl or haloalkyl;

R$_8$ may be selected from the group consisting of optionally substituted alkyl, cycloalkyl, cycloalkylalkyl, heterocycle, heteroaryl, heteroarylalkyl, alkylsulfamoyl, amino, monoalkylamino, dialkylamino, dialkylaminoalkylamino, alkoxy, and aryloxy; and the pharmaceutically acceptable salts thereof. Furthermore, R$_8$ may be a substituent selected from the group consisting of methyl, ethyl, propyl, isopropyl, cyclopentyl, cyclopropyl, cyclopropylmethyl, methylsulfamoyl, methylamino, trifluoromethyl, and 2-ethoxyethyl.

In additional embodiments of the invention, the pharmaceutical compositions may include at least one USP7i of formula IV:

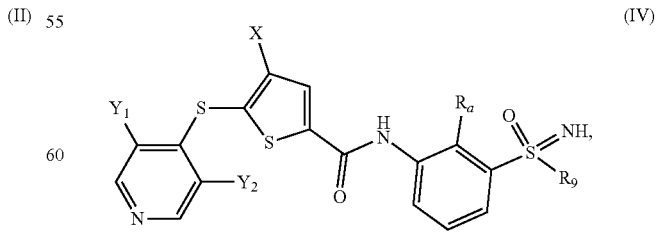

(IV)

wherein X is nitro or cyano;
Y$_1$ and Y$_2$ may be the same or different and represent halogen, alkyl or haloalkyl;

R₉ may be selected from the group consisting of optionally substituted alkyl, cycloalkyl, heterocycle, heteroaryl, heteroarylalkyl, alkoxy, and aryloxy; R_a may be hydrogen, optionally substituted alkyl or optionally substituted cycloalkyl; and the pharmaceutically acceptable salts thereof. Furthermore, R₉ and R_a may be a substituent selected from the group consisting of methyl, ethyl, propyl, isopropyl, cyclopentyl, cyclopropyl, cyclopropylmethyl, and trifluoromethyl.

In preferred embodiments, R9 in formula (IV) is selected from the group consisting of optionally substituted alkyl, cycloalkyl, heterocycle, heteroaryl and heteroarylalkyl.

Furthermore, the pharmaceutical compositions of the invention may include at least one USP7i of formula V:

(V)

wherein X is nitro or cyano;

Y₁ and Y₂ may be the same or different and represent halogen, alkyl or haloalkyl;

R₁₀ and R₁₁ may be independently selected from the group consisting of H, halo, hydroxyl, and optionally substituted alkyl, aryl, alkoxy, aryloxy, heteroaryl, cycloalkyl, heteroarylalkyl, amino, monoalkylamino, dialkylamino, and dialkylaminoalkylamino; R12 may be hydrogen, optionally substituted alkyl or optionally substituted cycloalkyl; the dotted line represents a single bond or a double bond; Y represents O or NH; and the pharmaceutically acceptable salts thereof. In certain embodiments, Ra may be selected from the group of methyl, ethyl, propyl, isopropyl, cyclopentyl, cyclopropyl, cyclopropylmethyl, and trifluoromethyl. Furthermore, in specific embodiments, compounds of formula V include:

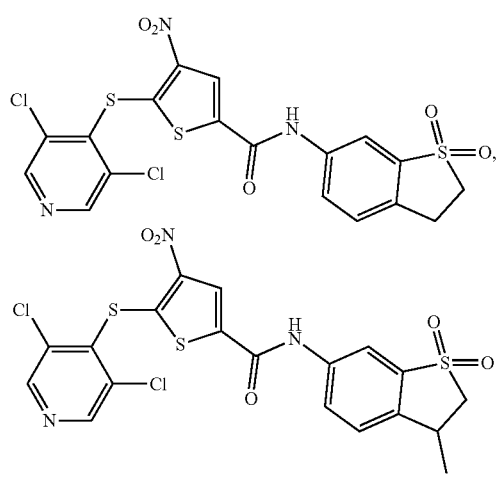

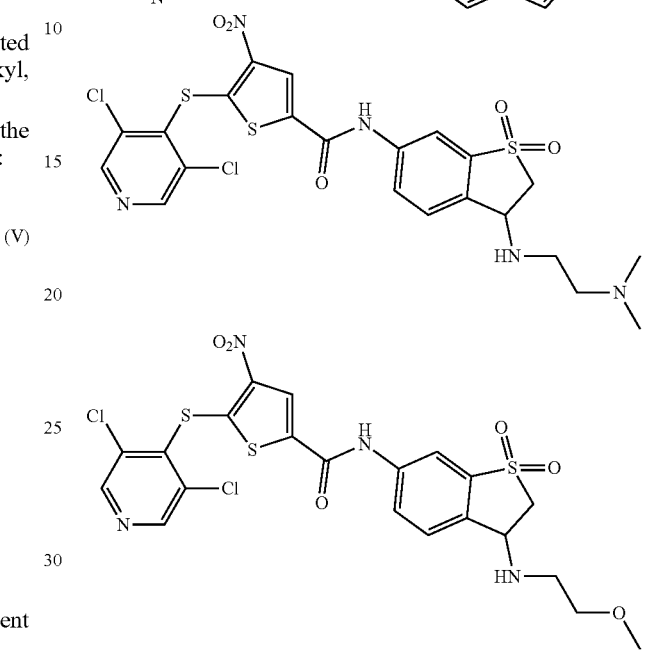

In a further embodiment, the pharmaceutical composition of the invention may include at least one USP7 inhibitor of formula VI:

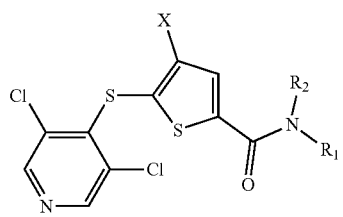

wherein X is nitro or cyano; R₁ represents an optionally substituted 1,1-dioxidotetryadro-2H-thiopyran-4-yl group, which may be fused to an optionally substituted aryl, cycloalkyl, heteroaryl or heterocyclic group; and R₂ represents hydrogen or optionally substituted alkyl.

The pharmaceutical compositions of the invention may include at least one USP7i of formula I, II, III, IV, V and/or VI formulated with at least one of a physiologically acceptable carrier, diluents and excipient. Each USP7i, or combination thereof, may be delivered as such, or as a prodrug, solvate, or a combination thereof.

In certain additional embodiments, the pharmaceutical compositions of the invention may include the administration of an anticancer vaccine, anticancer immunotherapy agents or another anti-cancer drug.

In another aspect, the present invention provides pharmaceutical compositions for treating a pathological condition in a patient in need thereof where treatment of the pathological condition is effected by inhibiting USP7.

In a further aspect, the present invention includes administering a pharmaceutical composition for treating cancer in a patient in need thereof and may, for example, provide a therapeutic effect by modulating immune system activity. More specifically, the pharmaceutical compositions of the invention may provide anti-cancer activity, for instance, due to their inhibition of USP7. The pharmaceutical compositions of the invention may include an amount of a USP7i that may be effective to reduce Treg cell activity and/or increase Teff cell activity.

Certain compounds encompassed within the present invention also inhibit USP47, which regulates DNA base excision repair by controlling the deubiquitination of DNA POL β which promotes the repair of DNA strand breaks, whose repair often leads to defective DNA and cancer. It has been found that knockdown of USP47 reduces tumor cell proliferation and enhances the cytotoxicity activity of some chemotherapeutic agents [5]. As described herein, certain compounds of the invention inhibit USP7 and may further inhibit tumor growth by modulating immune system activity.

BRIEF DESCRIPTION OF THE DRAWINGS

The foregoing summary and the following detailed description of the exemplary embodiments of the present invention may be further understood when read in conjunction with the appended drawings, in which.

Figure 1:
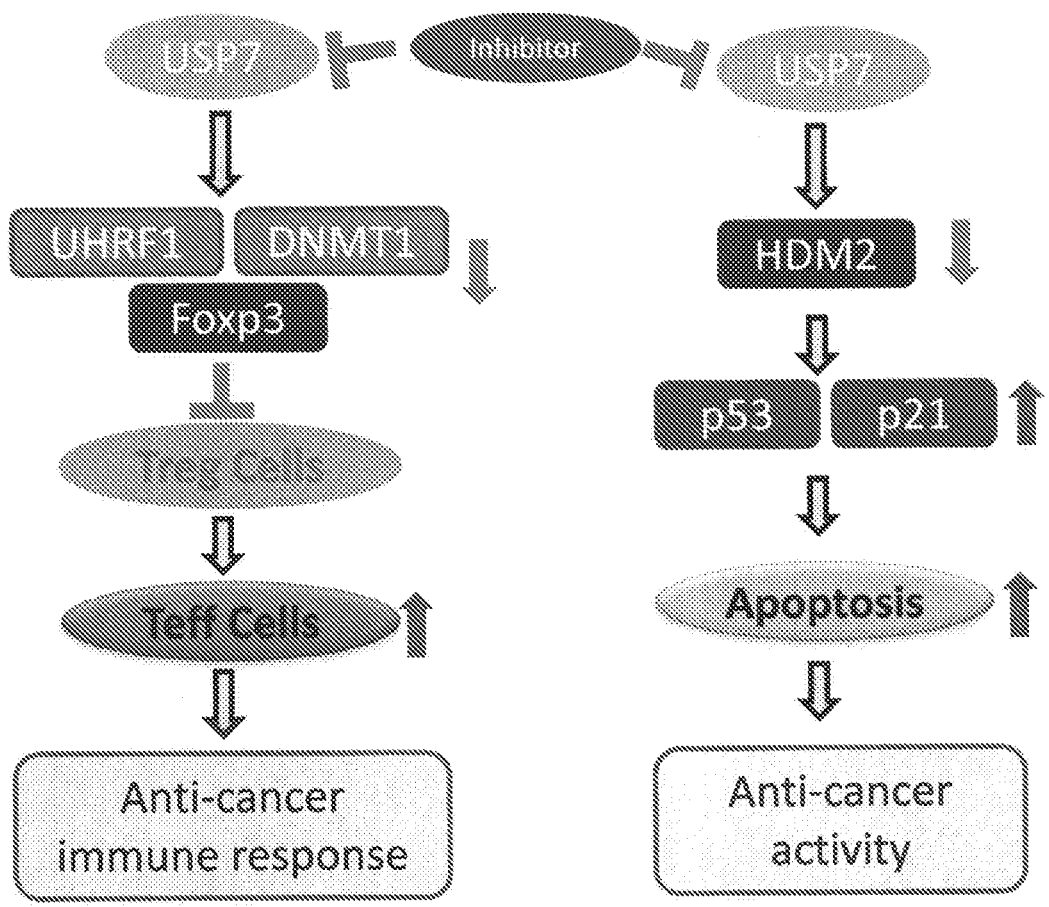
FIG. 1 schematically illustrates, without being limited to any one theory of the invention, a general description of the multimodal anti-tumor activity of USP7 inhibitors. In one mode, identified as anti-cancer activity in FIG. 1, treatment with a USP7 inhibitor results in downregulation of oncogenic substrates such as HDM2 resulting in upregulation of tumor suppressors including p53 and p21 thereby leading to apoptosis and inhibition of tumor growth.

In another mode, identified as anti-cancer immune response in FIG. 1, USP7 inhibitor treatment results in downregulation of USP7 substrates including DNMT1, UHRF1 and FOXP3 leading to inactivation and or downregulation of regulatory T cells, also known as Tregs, and activation of T effector cells. Additionally, USP7 inhibitor mediated inactivation and or downregulation Tregs could lead to activation of NK cells and B cells [7, 8].

Figure 2:
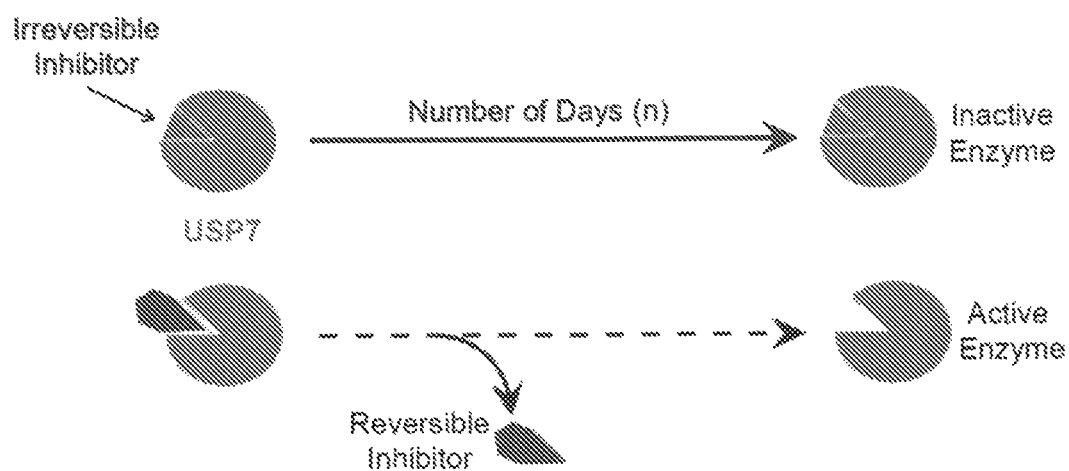

FIG. 2 schematically illustrates the difference between irreversible inhibitors and reversible inhibitors of USP7. An irreversible inhibitor may engage the target enzyme in a tight and or covalent interaction mode resulting in enzyme inhibition for prolonged period of time. A reversible inhibitor is in equilibrium such that it is easily disengaged from the target enzyme resulting in restoration of enzyme activity in relatively shorter period of time.

Figure 3B:
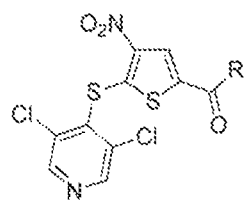

FIG. 3A-FIG. 3C provide tables setting forth representative examples of thiophene compounds of the invention having USP7 inhibitory activity.

Figure 4:
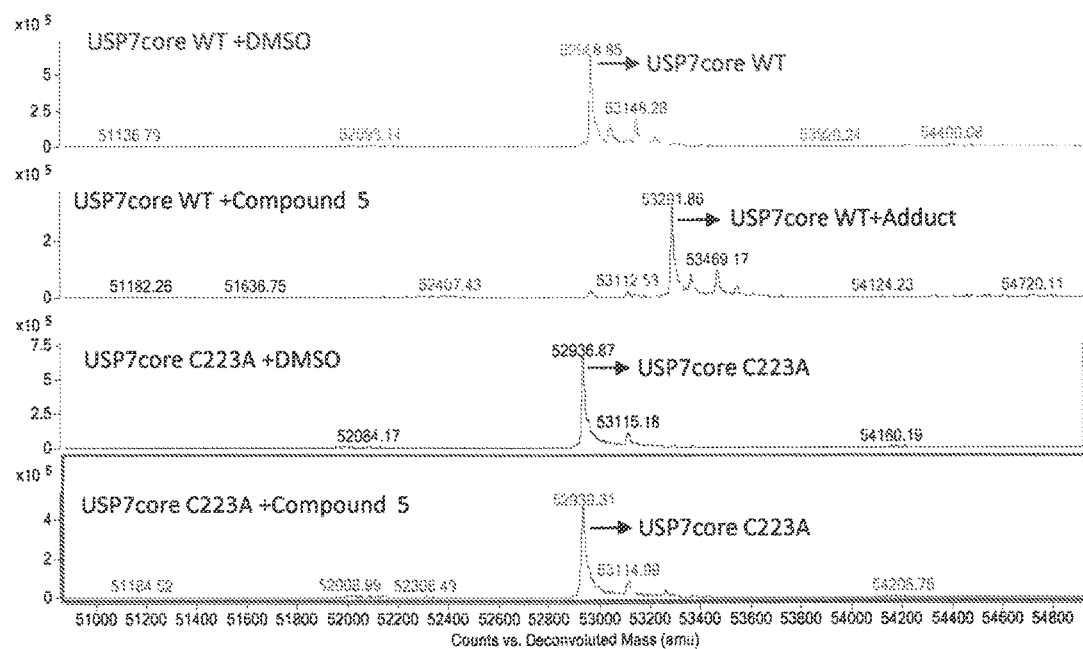

FIG. 4 provides data showing an example of the covalent irreversible nature of disclosed USP7 inhibitors. 5 μM purified USP7core WT or active site cysteine mutant C223A were incubated with 100 μM Compound 5 or DMSO at room temperature for 4 hrs, and then the protein/compound reaction products were mixed with equal volume of 0.1% Trifluoroacetic acid (TFA) before LC-MS injection. The samples were analyzed by reverse-phase liquid chromatography coupled to UV and MS detection (Agilent, 6220 Accurate-Mass Time-of-Flight (TOF) LC/MS). While the wild type USP7 core formed a covalent adduct with compound 5, the active site mutant USP7 core C223A failed to form an adduct indicating that this active site cysteine is necessary for the adduct formation.

Figure 5A:
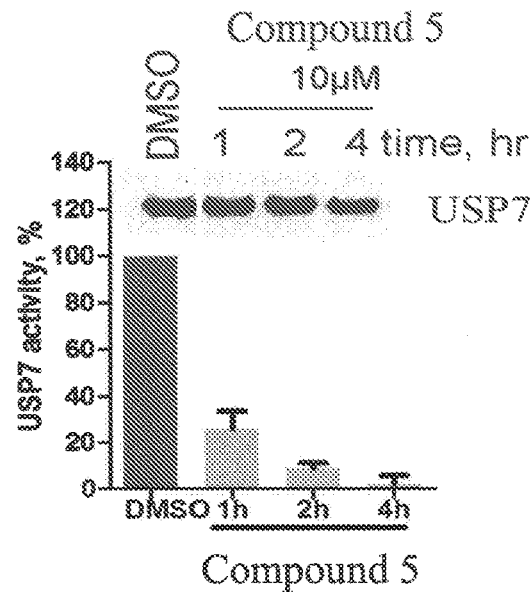
Figure 5B:
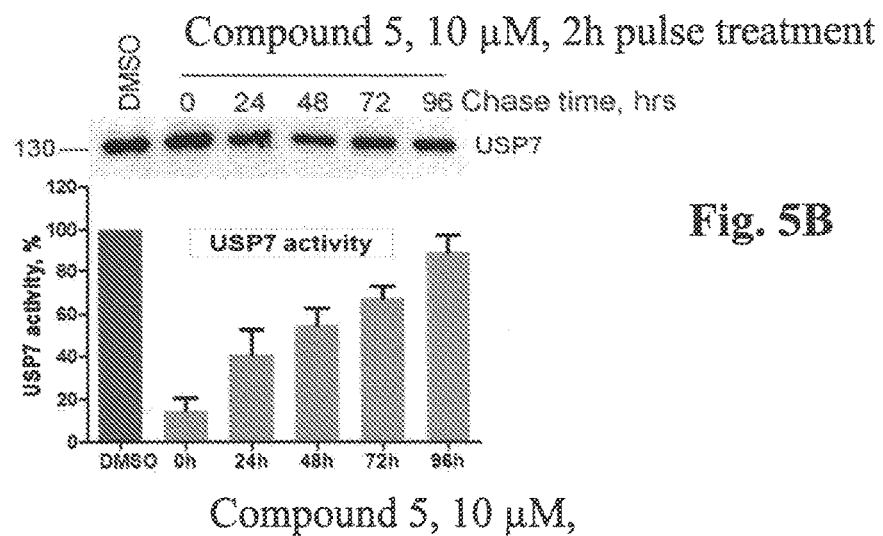
Figure 5C:
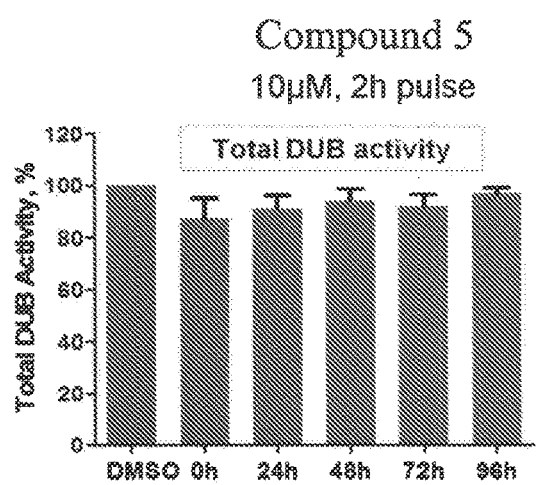

FIG. 5A-FIG. 5C graphically illustrate examples of the disclosed USP7 inhibitors of the invention that are irreversible inhibitors. Jurkat cells were treated with 10 μM USP7i for indicated time period (FIG. 5A) or pulse treated for 2 h with 10 μM compound 5 (FIG. 5B), washed and incubated for the indicated time period followed by DUB activity measurement of immunoprecipitated USP7 as well as total cell lysate (FIG. 5C) using Ub-EKL assay as described previously (U.S. Pat. No. 8,680,139). A portion of the immunoprecipitated USP7 is separated on 10% SDS-PAGE and immunoblotted with anti-USP7 antibody to detect the level of USP7 protein (shown at the top of graphs in FIG. 5A and FIG. 5B).

Figure 6:
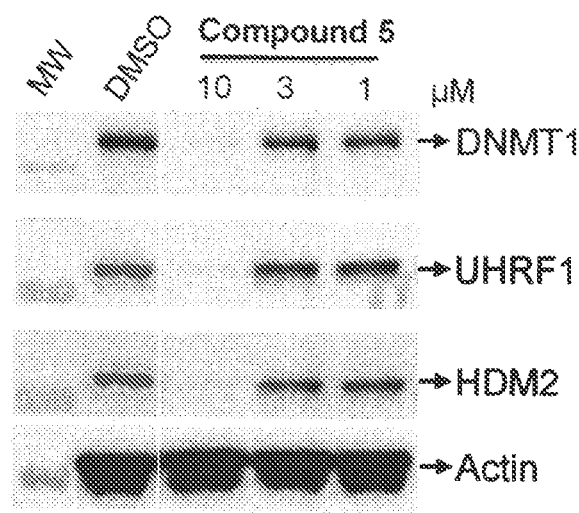

FIG. 6 graphically illustrates a decrease in USP7 oncogenic substrates DNMT1, UHRF1 and HDM2 levels in Jurkat cells treated with the USP7i compound 5. 20 μg total cell lysates from each samples were separated on 10% SDS-PAGE and immunoblotted with antibodies against DNMT1, UHRF1, HDM2 and Actin (loading control).

DETAILED DESCRIPTION OF THE INVENTION

Tumors have distinctive properties of growth, invasion and metastasis, and have the ability to evade immune mediated destruction. Although the precise mechanisms of cancer immune evasion are not very well understood, several contributing factors, including lack of sufficient antigenicity, have been described. In addition, tumors that possess sufficient antigenicity employ an elaborate network of cellular and tumor microenvironmental factors to attenuate and suppress anti-tumor immune responses. Recruitment and activation of regulatory T cells (Tregs) by tumors is now recognized as a critical component of immune evasion. While tumor-infiltrating CD8 T cells are associated with improved clinical outcomes, accumulation of Foxp3+ Treg cells in tumors and/or draining lymph nodes has a negative prognostic effect for many solid tumors [9], including lung (NSCLC), ovary, endometrium, cervix, breast, prostate, head and neck, esophagus and stomach, liver, pancreas, colon, and skin (melanoma) cancers . A need exists for targeting inhibitory molecules expressed by tumor cells and immune cells, e.g., CTLA-4, PD-1 and PD-L1, and many immune-checkpoint antibodies (Abs) probably block the activity of Treg cells; there are, however, no Treg-specific Abs [10]. Monoclonal antibody (mAb) targeting of CTLA-4 in patients with melanoma is commonly accompanied by hallmarks of autoimmunity, e.g., colitis and dermatitis. In a pooled analysis of 14 phase I-III studies, 64% of patients receiving various doses of ipilimumab (anti-CTLA-4) experienced immune-related adverse effects. Moreover, patients receiving dual therapy with anti-PD-1 mAb plus ipilimumab had a 93% incidence of adverse events; these were severe in 49% of patients, and led to discontinuation of therapy in 21% of them [11].

Foxp3+ Tregs negatively impact T cell proliferation and inhibition of Tregs is an emerging strategy to promote host anti-tumor T cell responses (see FIG. 1). Foxp3 is expressed by CD4+CD25+ Tregs, and gain-of-function, over-expression, and analysis of Foxp3-deficient Scurfy (sf) mice show Foxp3 is essential to the development and maintenance of murine Tregs. Scurfy mice experience lethal autoimmunity, as do humans with Foxp3 mutations unless treated (e.g., by immunosuppression or marrow transplant). By contrast, over-expression of murine Foxp3 gene leads to hypocellular lymphoid tissues with fewer T cells and a hypoactive immune state. Hence, control of Foxp3 levels within a certain range is required for optimal immune functions and survival. Experimentally, depletion of Foxp3+ Tregs has proven of mixed benefit in tumor bearing hosts. Strategies employed have included the use of: CD4 mAb or cyclophosphamide; direct targeting using anti-CD25 mAbs or anti-CTLA4 mAbs; diphtheria or pseudomonas toxin conjugated to IL-2, or small molecule inhibitors or mAbs to disrupt signals promoting Treg development, recruitment or function. Use of these agents typically has only modest efficacy that may reflect co-targeting of activated effector T cells, increased rates of autoimmunity, inflammatory toxicity, and transient efficacy with rebound of Treg numbers.

Protein ubiquitination and subsequent proteasome degradation are important steps in cell cycle progression, signal transduction and physiological regulation of multiple cellular processes, such as the elimination of damaged, abnormal or misfolded proteins. Protein ubiquitination is antagonized by deubiquitinating enzymes (DUB s), which play a critical role in regulating a diverse set of biological processes. In particular, the DUB USP7 plays a key role in regulating the stability of the RING-finger E3 ligase MDM2 (and its human homolog HDM2). HDM2 binds to the tumor suppressor p53 and facilitates its degradation by the proteasome by polyubiquitinating p53. Data from knockdown and knockout experiments demonstrate that HDM2 is unstable in the absence of functional USP7, the net consequence of inhibiting USP7 thus being enhanced stability of p53. In addition to the proven link between USP7 and p53, the inhibition of USP7 is predicted to impact tumor cell survival in a p53 independent manner. For example, USP7 has additional targets, such as Foxp3,UHRF1, DNMT1, the adaptor protein claspin and the anti-proliferative factors PTEN and FOXO4. Thus, inhibiting USP7 has the potential to negatively regulate tumor proliferation in p53+/+, p53mut, or p53−/− tumors and USP7 represents an attractive cancer target [4]. The confirmation of the role of USP7 in oncogenesis, wherein USP7 is overexpressed in multiple myeloma, leukemia, prostate, bladder, colon, liver, lung, and prostate cancer, validates USP7 as a compelling target for the treatment of cancer.

Most notably, USP7 substrates UHRF1, DNMT1 and Foxp3 have also been implicated in regulating Treg cell numbers and their immunosuppressive functions. Foxp3 is the lineage specific transcription factor of Treg cells and mutation, deletion or downregulation of Foxp3 results in Treg impairment and autoimmune disorders [12, 13]. Treg specific deletion of DNMT1 causes reduction in extrathymic Treg levels and leads to lethal autoimmunity [14]. T cell specific deletion of UHRF1 resulted in defects in the development of colonic Tregs [15]. Thus several studies have established a clear role of these USP7 substrates in modulating Treg levels and functions. Inhibiting or reducing the function of USP7 either by knocking-down or by using small molecule inhibitors of USP7 causes downregulation of UHRF1, DNMT1 and Foxp3 protein levels [5, 6, 16]. Therefore inhibition of USP7 may impair Treg functions and activate Teff cells.

Further, DNA base excision repair (BER) is an essential cellular process required for genomic stability, and dysregulation of BER is linked to premature aging, increased rate of mutagenesis, and cancer. The cytoplasmic ubiquitin-specific polymerase USP47 has been identified as the major enzyme involved in deubiquitination of the key BER DNA polymerase (Pol β), and USP47 is required for the stability of newly synthesized cytoplasmic Pol β that is used as a source of nuclear Pol β involved in DNA repair. Knockdown of USP 47 causes an increased level of ubiquitinated Pol β, decreased levels of Pol β, and a subsequent deficiency in BER leading to accumulation of DNA strand breaks and decreased cell viability in response to DNA damage. Taken together, these data demonstrate an important role for USP47 in regulating DNA repair and maintaining genome integrity. Therefore, both USP7 and USP47 represent important targets in the development of cancer therapeutics [17]

Accordingly, the compound utilized in the compositions of the invention represent inhibitors of USP7 and may be compounds that are effective to reduce Treg cell activity and/or increase Teff cell activity. In certain aspects, the compounds of the invention may also be inhibitors of USP47. Moreover, the preferred compounds of the invention may be irreversible inhibitors of USP7.

As used herein, an "irreversible inhibitor" is a compound that covalently binds a target protein through a substantially permanent covalent bond and inhibits the activity of the target protein for a period of time that is longer than the functional life of the protein. Irreversible inhibitors are usually characterized by time dependency. Recovery of target protein activity when inhibited by an irreversible inhibitor is dependent upon new protein synthesis. Suitable methods for determining if a compound is an irreversible inhibitor are well-known in the art through kinetic analysis. As used herein, a "reversible inhibitor" is a compound that reversibly binds a target protein and inhibits the activity of the target protein. Recovery of target protein activity when inhibited by a reversible inhibitor can occur by dissociation of the reversible inhibitor from the target protein.

The compounds and pharmaceutical compositions of the invention (e.g., USP7 inhibitors) may include those compounds of formulas I, II, III, IV, and/or V. Particularly preferred compounds of the invention are those described in the tables of FIGS. 3A, 3B and 3C.

The term "alkyl" refers to a saturated, branched or linear hydrocarbon group. Typical alkyl groups include, but are not limited to, methyl, ethyl, propyl, isopropyl, butyl, isobutyl, t-butyl, pentyl, isopentyl, hexyl and the like. In preferred embodiments, the alkyl groups are $(C_1-C_6)$ alkyl, with $(C_1-C_3)$ being particularly preferred. "Lower alkyl" refers to $C_1-C_6$ alkyl. "Substituted alkyl," as used herein, refers to an alkyl group that may be substituted with one or more functional groups which are attached commonly to such chains, such as, hydroxy, halogen, mercapto or thio, cyano, alkylthio, carboxy, carbalkoxy, amino, nitro, alkoxy, or optionally substituted, alkenyl, alkynyl, heterocyclyl, aryl, heteroaryl, and the like to form alkyl groups such as perfluoro or partially fluorinated alkyl, and the like.

"Alkenyl" refers to an unsaturated branched or linear hydrocarbon group containing a carbon-carbon double bond. Typical alkenyl groups include, but are not limited to, ethenyl, propenyl, n-butenyl, i-butenyl, 3-methylbut-2-enyl, n-pentenyl, heptenyl, octenyl, nonenyl, decenyl. "Lower alkenyl" refers to $C_2-C_6$ alkenyl.

The term "halogen" or "halo" as used herein alone or as part of another group refers to chlorine, bromine, fluorine, and iodine.

As used herein, the term "heteroatom," unless otherwise indicated, may refer to O, N, S, Si, P, or B.

The term "alkoxy" refers to alkyl-O—, in which alkyl is as defined above.

Unless otherwise indicated, the term "cycloalkyl" or "cycloalkylene," as used herein, alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described below for aryl, which include cyclopropyl, cyclobutyl, cyclopentyl, cyclohexyl, cycloheptyl, cyclooctyl, cyclodecyl, cyclododecyl and cyclohexenyl. "Substituted cycloalkyl," as used herein, refers to a cycloalkyl group that may be substituted with 1 or more substituents such as halogen, alkyl, substituted alkyl, alkoxy, hydroxy, aryl, substituted aryl, aryloxy, cycloalkyl, alkylamido, alkanoylamino, oxo, acyl, arylcarbonylamino, amino, nitro, cyano, thiol and/or alkylthio and/or any of the substituents included in the definition of "substituted alkyl."

"Alkylthio" refers to an alkyl-S- group wherein alkyl is as previously described. Exemplary alkylthio groups include methylthio, ethylthio, i-propylthio and heptylthio.

"Monoalkylamino" refers to an —NHR' group wherein R' may represent H, optionally substituted lower alkyl or phenyl. Exemplary monoalkylamino groups include methylamino and ethylamino.

"Dialkylamino" refers to an —NR'R" group wherein each of R' and R", wherein R' and R" independently represent H, optionally substituted lower alkyl or phenyl. Exemplary dialkylamino groups include ethylmethylamino, dimethylamino and diethylamino.

Unless otherwise indicated, the term "aryl" or "Ar," as used herein, alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, such as aryl, cycloalkyl, heteroaryl or cycloheteroalkyl rings or substituted forms thereof. "Substituted aryl," as used herein, refers to an aryl group that may be substituted with one or more functional groups, such as halo, alkyl, haloalkyl (e.g., trifluoromethyl), alkoxy, haloalkoxy (e.g., difluoromethoxy), alkenyl, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, alkylcarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are optionally substituted alkyl, aryl or any of the other substituents mentioned in the definitions), thiol, alkylthio, arylthio, heteroarylthio, arylthioalkyl, alkoxyarylthio, alkylaminocarbonyl, arylaminocarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl sub stituents set out herein.

Unless otherwise indicated, the term "alkynyl," as used herein, by itself or as part of another group refers to straight or branched chain of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" as used herein, refers to an alkynyl group that may be substituted with one or more substituents, such as the substituents included above in the definition of "substituted alkyl" and "substituted cycloalkyl."

Unless otherwise indicated, the term "heteroaryl," as used herein, alone or as part of another group, refers to a 5- to 7-membered aromatic ring which includes 1, 2, 3 or 4 hetero atoms such as N, O, or S, and such rings fused to an aryl, cycloalkyl, heteroaryl or heterocyclic ring (e.g. benzothiophenyl, indolyl), and includes possible N-oxides. "Substituted heteroaryl," as used herein, refers to a heteroaryl group that may be substituted with 1 to 4 substituents, such as the substituents included above in the definition of "substituted alkyl" and "substituted cycloalkyl. Substituted heteroaryl also includes fused heteroaryl groups which include, for example, quinoline, isoquinoline, indole, isoindole, carbazole, acridine, benzimidazole, benzofuran, isobenzofuran, benzothiophene, phenanthroline, purine, and the like.

The term "heterocyclo", "heterocyclic" or "heterocycle" as used herein, for example refers to an optionally substituted stable 5- to 7-membered monocyclic ring which may be saturated or unsaturated, and which consists of carbon atoms and from one to four heteroatoms selected from N, O or S, and such rings fused to an aryl, cycloalkyl, heteroaryl or heterocyclic ring (e.g., 1,1-dioxidothiocroman-4-yl or 4,4-dioxidoherahydropyrano [3,4-b] [1,4] thiazin-1(5H)-yl) and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Heterocycles include, for example, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridinyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinylsulfoxide, thiamorpholinylsulfone, and oxadiazolyl.

Unless otherwise described herein, the term "optionally substituted" indicates that a chemical moiety referred to, for example, alkyl, aryl, heteroaryl, may be unsubstituted or substituted with one or more groups including, for example, lower alkyl, alkenyl, alkynyl, cycloalkyl, arylalkyl, aryl, heterocycle, heteroaryl, hydroxyl, amino, monoalkylamino, dialkylamino, alkyl-S(O)$_n$, cycloalkyl-S(O)$_n$, aryl-S(O)$_n$, alkoxy, halogen, carboxy, and carbalkoxy; and n=0-2.

"Therapeutically effective amount" refers to an amount of a compound of the present invention effective to (1) inhibit or treat the initiation, growth and/or progression of a cancerous tissue and/or cells, and (2) reduce Treg cell activity and/or increase Teff cell activity. The term "treat", "treatment" or "treating" when used herein in relation to cancer therapy refers to the administration of a compound of the invention as a monotherapy, or part of a combination therapy, for inhibiting the growth or metastasis of any cancerous tissue or cells that may exist in a patient and/or stimulating regression thereof, including reducing the size and/or number of such cancers and/or inducing the death of cancerous tissue and/or cells. Effective treatment may also be manifested by providing a patient relief from or alleviation of the clinically recognized symptoms or other diagnostic indicators of a specific cancer. The compounds and compositions described herein may also be used to delay the onset or prevent the occurrence of a recited cancer in a patient.

"Pharmaceutically acceptable" refers to those compounds, materials, compositions, and/or dosage forms which are, within the scope of sound medical judgment, suitable for contact with the tissues of human beings and non-human animals without excessive toxicity, irritation, allergic response, or other adverse complications commensurate with a reasonable benefit/risk ratio.

The compounds of formula I, II, III, IV, V and/or VI may be in the form of pharmacologically acceptable salts, their solvates, and may be in one or more crystal forms.

"Pharmaceutically acceptable salts" refers to salts of compounds of the present invention (e.g., compounds of formulas I, II, III, IV, V and/or VI) derived from the combination of such compounds with non-toxic acids or bases.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic compounds such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included within the scope of this invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvates can be from the solvent of crystallization, inherent in the solvent of preparation or crystallization, or adventitious to such solvent. Such solvates are also within the scope of the present invention.

As the compounds of the invention may contain charged side chains or termini, they may be included in any of the above-described formulations as the free acids or bases or as pharmaceutically acceptable salts. Pharmaceutically acceptable salts tend to be more soluble in aqueous and other protic solvents than are the corresponding free acid or base forms.

According to another aspect, the products may be converted to a dosage form by combining with acceptable excipients, and in some instances combined with another drug to achieve enhanced effects. In some instances the drugs may be in the form of a prodrug.

The present invention also encompasses pharmaceutically acceptable prodrugs of the above-described compounds. As used herein, "prodrug" refers to any compound which is converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be produced for delivery in prodrug form. Conventional procedures for the selection and preparation of suitable prodrug derivatives are described, for example, in *Prodrugs*, Sloane, K. B., Ed.; Marcel Dekker: New York (1992).

As will be apparent to those skilled in the art, the compounds of the present invention may have one or more chiral centers, and in that case, exist in various stereoisomeric forms. The compounds of the present invention encompass all such optical isomers, diastereomers and enantiomers. The compounds may be prepared as a racemic mixture or racemate and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms from a mixture of enantiomers. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

For example, compounds 20 and 22 of this invention include a stereocenter, but may be provided as racemates. However, these compounds may be resolved to provide the respective stereoisomers using one or more of the separation strategies provided above. In addition, the therapeutic activity of the tested racemates (e.g., compounds 20 and 22 are each assumed to derive from a single potent stereoisomer. Therefore, the single stereoisomer from the racemic mixture is assumed to be twice as potent as the respective racemate. Nevertheless, the present invention expressly encompasses the R and S stereoisomers of the invention (e.g., compounds 20 and 22) in addition to the racemic mixture thereof.

Any compound of the invention may be administered to a subject by itself, or in the form of a pharmaceutical composition. Pharmaceutical compositions comprising the compounds of the invention may be manufactured by means of conventional mixing, dissolving, granulating, drageemaking, levigating, emulsifying, encapsulating, entrapping or lyophilizing processes. Pharmaceutical compositions may be formulated in conventional manner using one or more physiological acceptable carriers, diluents, excipients, or auxiliaries which facilitate processing of the compounds into preparations which can be used pharmaceutically. A specific formulation method will be dependent upon the route of administration chosen.

The terms "subject" and "patient" are used interchangeably herein to refer to a warm blooded animal such as a mammal, including a human, which is afflicted with, or has the potential to be afflicted with one or more diseases and/or conditions described herein.

For topical administration the compounds of the invention may be formulated as solutions, gels, ointments, creams, suspensions etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hank's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the compounds with pharmaceutically acceptable carriers well known in the art. Such carriers enable the compounds of the invention to be formulated as tablets, pills, dragees, capsules, liquid gels, syrups, slurries, suspensions and the like, for oral ingestion by a patient to be treated. For oral solid formulations, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium, carboxymethylcellulose, and/or polyvinylpyrrolidone (PVP); granulating agents; and binding agents. If desired, disintegrating agents may be added, such as the cross-linked polyvinylpyrrolidine, atgar, or alginic acid or a salt thereof such as sodium alginate.

If desired, solid dosage forms may be sugar-coated or enteric-coated using standard techniques.

For oral preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver the compounds of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. A variety of sustained-release materials have been established and are well known by those skilled in the art. Sustained-release capsules may, depending on their chemical nature, release the compounds for a few weeks up to over 100 days.

The compounds of the invention can be used to manufacture a medicament in a suitable dosage unit form for ease of administration and uniformity of dosage. "Dosage unit form", as used herein, refers to a physically discrete unit of an anticancer and/or immune system modulating agent appropriate for the patient to be treated. Each dosage should contain the quantity of active material calculated to produce the desired therapeutic effect either as such, or in association with the selected pharmaceutical carrier medium and/or the supplemental active agent(s), if any.

For systemic administration, a therapeutically effective dose can be estimated initially from in vitro assays. For example, a dose can be formulated in animal models to achieve a circulating concentration range that includes the $IC_{50}$ as determined in cell culture (i.e. the concentration of test compound that inhibits 50% of USP7). Such information can be used to more accurately determine useful doses in humans.

Initial dosages can also be estimated from in vivo data. e.g. animal models, using techniques that are well known in the art. One having ordinary skill in the art could readily optimize administration to humans based on animal data.

Dosage amount and interval may be adjusted individually to provide therapeutically effective serum levels of the compounds described herein. Usual patient dosages for administration by injection range from about 0.1 to 50 mg/kg/day, preferably from about 0.5 to 5 mg/kg/day. Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on a number of factors, including age, weight and gender of the subject being treated, the severity of the disease or condition, the manner of administration and the judgment of the prescribing physician or other medical specialist. However, an effective amount of compound of the present invention for the treatment of cancer should be in the range of 0.1 to 100 mg/kg body weight of recipient (mammal) per day. More usually the effective amount should be in the range of 0.1 to 10 mg/kg body weight per day. The amount per day would usually be from 3 to 3000 mg. This amount maybe given in a single dose per day or in a number (such as two, three, four, five, or more) of sub-doses per day such that the total daily dose is the same. An effective amount of salt, solvate, or physiologically functional derivative thereof, may be determined as a portion of the effective amount of the compound of the present invention per se.

Preferably, a therapeutically effective dose of the compound described herein will provide therapeutic benefit without causing appreciable toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The ratio of the median lethal dose to the median effective dose is the therapeutic index, used in quantitative comparison of drugs. Compounds which exhibit high therapeutic indices are preferred. The data obtained from these cell culture assays and animal studies can be used in formulation of a dosage range that is not toxic for use in humans. The dosage of the compounds described herein lies preferably within a range of circulating concentrations that include the effective dose with little or no toxicity. The dosage may vary within this range depending on the dosage form employed and the route of administration utilized. The exact formulation, route of administration and dosage can be chosen by the individual physician in view of the patient's condition. (See, e.g., Fingl et al., In: The Pharmacological Basis of Therapeutics, Ch. 1, p.1, 1975).

Accordingly, the compounds used in practicing this invention are typically administered to a patient in the form of a pharmaceutical composition or formulation. Such pharmaceutical compositions may be administered to the patient by any acceptable route of administration including, but not limited to, oral, nasal (including inhalation), topical (including transdermal) and parenteral modes of administration. It will be understood that any form of the compounds of this invention (i.e., free base, pharmaceutically acceptable salt, solvate, etc.) that is suitable for the particular mode of administration can be used in the pharmaceutical compositions discussed herein.

The compounds of the present invention are useful, inter alia, as therapeutic agents for the treatment of cancer. Particularly, the compounds have demonstrated activity as USP7 inhibitors and may be modulators of immune system activity by reducing Treg cell activity and increasing or amplifying Teff cell activity. In one embodiment, the present invention provides a compositions for treating or preventing diseases and disorders, such as the cancers disclosed herein, which may include administering to a subject in need of such treatment or prevention a therapeutically effective amount of a compound of the present invention (e.g., one or more compounds of formulas I, II, III, IV, V and VI).

In an additional embodiment, the present invention provides a method for inhibiting the enzyme USP7 activity and modulating immune system activity as described herein comprising providing a compound of the present invention (e.g., a compound of formulas I, II, III, IV, and/or V) in an amount sufficient to result in effective inhibition. The compounds of the present invention can be administered to treat cancer, including multiple myeloma, leukemia, prostate cancer, breast cancer, bladder cancer, colorectal cancer, non-small cell lung cancer, CNS cancer, melanoma, ovarian cancer, renal cancer, or osteosarcoma.

As previously mentioned, the compounds of the invention may be administered for the treatment of a cancer in a combination therapy with other suitable treatment modalities. In the case of cancer, such other suitable treatment modalities may include, without limitation, administration of radiation therapy, e.g., gamma radiation therapy. Other suitable treatment modalities may include, for example, administering to a patient in combination with a USP7 inhibitor, as described herein, and an anticancer vaccine, an anticancer immunotherapy agent, anticancer immunomodulatory agent, an additional anticancer therapeutic, or a combination thereof.

Anticancer vaccines may include, for example, Gardasil and Cervarix (prophylactic) and Sipuleucel-T/Provenge (therapeutic).

Anticancer immunotherapy agents may include, for example, Alemtuzumab, Ipilimumab, Nivolumab, Pembrolizumab, Rituximab, Nivolumab, Interferon, and Interleukin.

Anticancer immunomodulatory agents may include for example, thalidomide, lenalidommide, and pomalimomide Additional anticancer therapeutics may include, for example, an alkylating agent, a tubulin inhibitor, a proteasome inhibitor, a topoisomerase inhibitor, a CHK1 inhibitor, a CHK2 inhibitor, a PARP inhibitor, doxorubicin, epirubicin, vinblastine, etopside, topotecan, bleomycin, and mytomycin c.

Alkylating agents may be selected from the group consisting of Dacarbazine, Procarbazine, Carmustine, Lomustine, Uramustine, Busulfan, Streptozocin, Altreamine, Ifosfamine, Chrormethine, Cyclophasphamide, Cyclophosphamide, Chlorambucil, Fluorouracil (5-Fu), Melphalan, Triplatin tetranitrate, Satraplatin, Nedaplatin, Cisplatin, Carboplatin, and Oxaliplatin.

Tubulin inhibitors may be selected from the group consisting of Taxol, Docetaxel, Vinblastin, Epothilone, Colchicine, Cryptophycin, BMS-347550, Rhizoxin, Ecteinascidin, Dolastin 10, Cryptophycin 52, and IDN-5109.

Proteasome inhibitors may be selected from the group consisting of Velcade (bortezomib), and Kyprolis (carfilzomib).

Topoisomerase I inhibitors may be selected from the group consisting of Irinotecan, Topotecan, and Camptothecins (CPT).

Topoisomerase II inhibitors may be selected from the group consisting of Amsacrine, Etoposide, Teniposide, Epipodophyllotoxins, and ellipticine.

CHK1 inhibitors may be selected from the group consisting of TCS2312, PF-0047736, AZ07762, A-69002, and A-641397.

PARP inhibitors may be selected from the group consisting of Olaparib, ABT-888, (veliparib), KU-59436, AZD-2281, AG-014699, BSI-201, BGP-15, INO-1001, ONO-2231 and the like.

Through combination therapy, reduction of adverse drug reaction and potentiation of anticancer activity are achievable by the combined effects of anticancer agents having different mechanisms of action, including reduction of the non-sensitive cell population; prevention or delaying of occurrence of drug resistance; and dispersing of toxicity by means of a combination of drugs having different toxicities.

When an anti-cancer agent used in combination has a particular medication cycle, it is preferable to establish an appropriate medication cycle for the compound of formulas I, II, III, IV, V and/or VI, and such anti-cancer agent, so that the desired effects are attained. Specifically, the frequency of administration, dosage, time of infusion, medication cycle, and the like, may be determined properly according to individual cases, considering the kind of anticancer agent, state of the patients, age, gender, etc.

In using the combination therapy of the present invention, the same dose as that usually given as a monotherapy or a slightly reduced dose (for example, 0.10-0.99 times the highest dose as a single agent) may be given through a normal administration route.

Treatment of patients using the above-described compounds and compositions will normally include medical follow-up to determine the therapeutic or prophylactic effect brought about in the patient undergoing treatment. Efficacy of the treatment may be assessed on the basis of tumor regression, e.g., reducing the size and/or number of neoplasms, inhibition of tumor metastasis, decrease in a serological marker of disease, or other indicator of an inhibitory or remedial effect.

The following examples describe the invention in further detail. These examples are provided for illustrative purposes only, and should in no way be construed as limiting the scope of the invention.

EXAMPLES

Example 1

Synthetic Procedures and Compound Characterization for Exemplary Compound 5-[(3,5-dichloropyridin-4-yl)sulfanyl]-N-[3-(methylsulfonyl)phenyl]-4-nitrothiophene-2-carboxamide (compound 5)

Generally, the compounds of this invention may be synthesized by the methods detailed in U.S. Pat. No. 8,680,139.

Exemplary compound 5 was prepared by the following scheme:

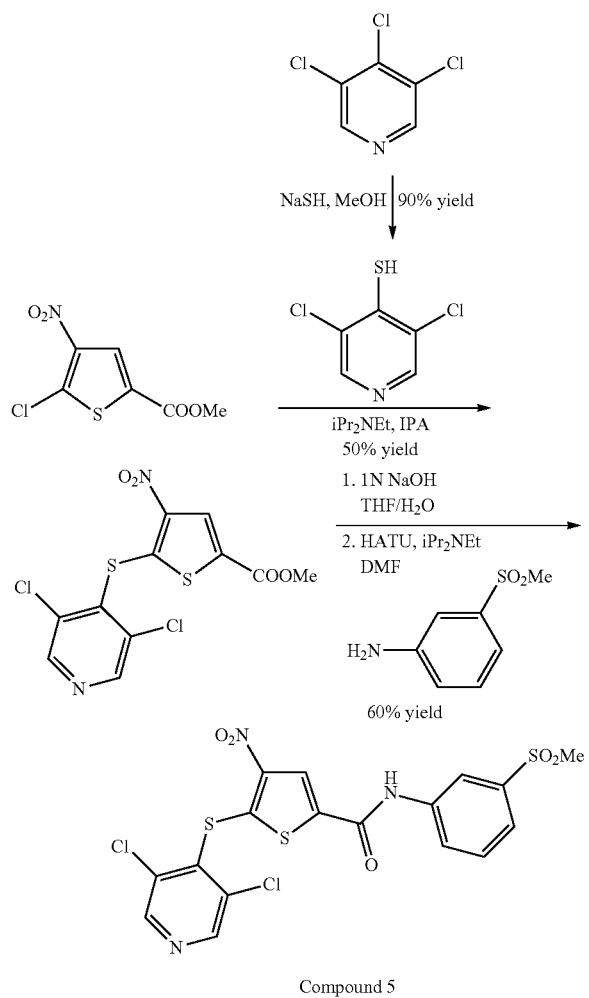

Compound 5

The compounds that were most active against USP7 were then examined for their effect on biomarkers.

Studies on the mechanism of the binding of some of the inhibitors showed that they acted as irreversible. Jurkat cells were exposed to compound 5 for 2 hours and the compounds were washed away followed by incubation for various time points. Cells were harvested, lysed and their USP7 immunoprecipitated and washed with buffer. Measurement of catalytic activity showed that after 48 hours only about 55% of the activity had returned, and after 72 hours 68% activity had returned.

Reagents and instruments: All reactions utilizing air- or moisture-sensitive reagents were performed in dried glassware under an atmosphere of dry Ar. Solvents were purchased from Aldrich and Acros without further purification. Reagents and chemicals were purchased from commercial sources with purity≥95% without further purification. Thin layer chromatography (TLC) was performed on EMD pre-coated plates (silica gel 60 F254, Art 5715, 0.25 mm) and compounds were visualized by fluorescence under UV light or by staining with phosphomolybdic acid. Column chromatography was performed on EMD Silica Gel 60 (230-400 mesh) using a forced flow of 0.5-1.0 bar. HRMS measurements were acquired by use of Agilent Accurate-Mass TOF LC/MS mass spectrometer and a Bruker microOTOF (ESI-TOF-MS) spectrometer.

Preparative HPLC: Samples were purified using a Gilson preparative HPLC system with 322 pump and UV/VIS 156. Method: Gemini C18 column 10 μm 30×100 mm with a linear gradient of 10-95% buffer B over 10 min with a flow rate of 20 mL/min (buffer A=0.1% TFA in $H_2O$; buffer B=0.1% TFA in $CH_3CN$). The eluent was monitored at 214 or 254 nm. The exact gradient used was determined by the elution behavior of the desired compound as assessed by prior analytical HPLC. Fractions containing the pure target compound were identified by analytical LCMS and were combined and lyophilized.

LC/MS conditions: Agilent 6220 TOF/LC-MS System; Column: RESTEK Viva C18 (5μm 2.1×50 mm); Mobile phase A: $H_2O$/0.05% TFA; Mobile phase B: $CH_3CN$/0.05% TFA; Flow: 0.4 ml/min; Gradient: 0 min 10% B, 0.25 min 10% B, 0.75 min 15% B, 1.75 min 55% B, 3.25 min 90% B, 3.5 min 90% B, 3.6 min 10% B, Stop 5 min; Column temperature: 50° C. All the target compounds have purities of >95% based upon LC/MS.

Synthesis of 5-[(3,5-dichloropyridin-4-yl)sulfanyl]-N-[3-(methylsulfonyl)phenyl]-4-nitrothiophene-2-carboxamide (compound 5)

O-(7-Azabenzotriazol-1-yl)-N,N,N',N'-tetramethyluronium hexafluorophosphate (HATU) (654 mg, 1.72 mmol, 2.0 equiv) and diisopropylethylamine (DIPEA) (0.45 mL, 2.58 mmol, 3.0 equiv) were added to a solution of 5-[(3,5-Dichloro-4-pyridinyl)sulfanyl]-4-nitrothiophene-2-carboxylic acid (300 mg, 0.86 mmol) in 4 mL DMF while stirring at 0° C. and held at this temperature for twenty minutes. 3-Methylsulfonylaniline (161 mg, 0.94 mmol, 1.1 equiv) was added and the reaction was allowed to slowly warm to RT. After 4 h, the reaction mixture was diluted with EtOAc (200 mL) and washed with 1M HCl solution (100 mL) and brine (100 mL). The organic layer was dried over $Na_2SO_4$, filtered, and concentrated under vacuum. The residue was purified by preparative reverse phase HPLC using a linear gradient of 10-95% $CH_3CN$ over 15 min with a flow rate of 20 mL/min. After lyophilization, pure product (260 mg, 60%) was obtained as a light yellow solid. Rf=0.38 (Hexane/acetone 2:1); HRMS (ESI) (m/z) [MH]$^+$ calcd for $C_{17}H_{12}Cl_2N_3O_5S_3$, 503.9316, found 503.9340.

Example 2

Irreversible USP7 Inhibition in Cells and Biomarker Development

5μM purified USP7core WT or C223A were incubated with 100 μM of an exemplary compound of the present invention (for example, Compound 5) or DMSO at room temperature for 4 h, and then the protein/compound reaction products were mixed with equal volume of 0.1% Trifluoroacetic acid (TFA). The samples were analyzed by reverse-phase liquid chromatography coupled to UV and MS detection (Agilent, 6220 Accurate-Mass Time-of-Flight (TOF) LC/MS). Treatment of USP7core with compound 5 resulted in a covalent irreversible adduct formation in the wild type enzyme but not in the active site cysteine mutant enzyme.

Jurkat cells were incubated with an exemplary compound of the present invention (e.g., compound 5), washed, and incubated for an additional 0-96 h. USP7 was immunoprecipitated from lysates and USP7 activity measured. Incubation with inhibitor for 1 h resulted in significant inhibition of catalytic activity of isolated USP7 (FIG. 5A). Treatment with 10 μM compound 5 for 2 h resulted in prolonged inhibition of USP7 activity, even after 72 h (FIG. 5B). Such time dependent and long lasting effects on USP7 enzymatic activity strongly suggest irreversible/covalent inhibition. Total cell deubiquitinase activity can be performed to determine selectivity of these compounds (FIG. 5C). These experiments delineate a simple, powerful biomarker for determining the dose-efficacy relationship in the pre-clinical/clinical evaluation of irreversible USP7 inhibitors. Inhibitors were also tested in cells for effects on various PD markers, including three major USP7 substrates, DNMT1, UHRF1 and HDM2. USP7 inhibitors decreased DNMT1, UHRF1 and HDM2 in a dose dependent manner in Jurkat cells after 24 h treatment(FIG. 6).

Example 3

Synthetic Procedures and Compound Characterization for Exemplary Benzothiophene Analogs of the Invention [18]

Reagents and instruments: All reactions utilizing air- or moisture-sensitive reagents were performed in dried glassware under an atmosphere of dry Ar. Solvents were purchased from Aldrich and Acros without further purification. Reagents and chemicals were purchased from commercial sources with purity≥95% without further purification. Thin layer chromatography (TLC) was performed on EMD pre-coated plates (silica gel 60 F254, Art 5715, 0.25 mm) and compounds were visualized by fluorescence under UV light or by staining with phosphomolybdic acid. Column chromatography was performed on EMD Silica Gel 60 (230-400 mesh) using a forced flow of 0.5-1.0 bar. HRMS measurements were acquired by use of Agilent Accurate-Mass TOF LC/MS mass spectrometer and a Bruker microOTOF (ESI-TOF-MS) spectrometer.

Preparative HPLC: Samples were purified using a Gilson preparative HPLC system with 322 pump and UV/VIS 156. Method: Gemini C18 column 10 μm 30×100 mm with a linear gradient of 10-95% buffer B over 10 min with a flow rate of 20 mL/min (buffer A=0.1% TFA in $H_2O$; buffer B=0.1% TFA in $CH_3CN$). The eluent was monitored at 214 or 254 nm. The exact gradient used was determined by the elution behavior of the desired compound as assessed by prior analytical HPLC. Fractions containing the pure target compound were identified by analytical LCMS and were combined and lyophilized.

LC/MS conditions: Agilent 6220 TOF/LC-MS System; Column: RESTEK Viva C18 (5 μm 2.1×50 mm); Mobile phase A: $H_2O$/0.05% TFA; Mobile phase B: $CH_3CN$/0.05% TFA; Flow: 0.4 ml/min; Gradient: 0 min 10% B, 0.25 min 10% B, 0.75 min 15% B, 1.75 min 55% B, 3.25 min 90% B, 3.5 min 90% B, 3.6 min 10% B, Stop 5 min; Column temperature: 50° C. All the target compounds have purities of>95% based upon LC/MS.

Synthesis of 5-[(3,5-dichloropyridin-4-yl)sulfanyl]-N-(1,1-dioxo-benzothiophen-6-yl)-4-nitrothiophene-2-carboxamide (compound 15)

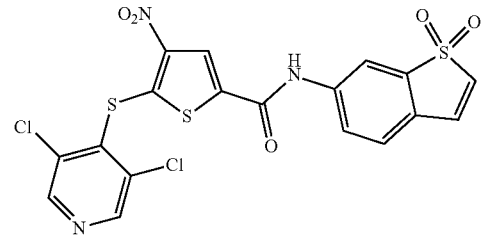 [SMILES: O=C(Nc1ccc2c(c1)S(=O)(=O)C=C2)c1cc([N+](=O)[O-])c(Sc2c(Cl)cncc2Cl)s1]

O-(7-Azabenzotriazol-1-yl)-N,N,N',N'-tetramethyluronium hexafluorophosphate (HATU) (217 mg, 0.57 mmol, 2.0 equiv) and diisopropylethylamine (DIPEA) (0.15 mL, 0.85 mmol, 3.0 equiv) were added to a solution of 5-[(3,5-Dichloro-4-pyridinyl)sulfanyl]-4-nitrothiophene-2-carboxylic acid (100 mg, 0.285 mmol) in 1 mL DMF while stirring at 0° C. and held at this temperature for twenty minutes. Benzo[b]thiophen-6-amine, 1,1-dioxide (56 mg, 0.314 mmol, 1.1 equiv) was added and the reaction was allowed to slowly warm to RT. After 4 h, the reaction mixture was diluted with EtOAc (100 mL) and washed with 1M HCl solution (50 mL) and brine (50 mL). The organic layer was dried over $Na_2SO_4$, filtered, and concentrated under vacuum. The residue was purified by preparative reverse phase HPLC using a linear gradient of 10-95% $CH_3CN$ over 15 min with a flow rate of 20 mL/min. After lyophilization, pure product (58 mg, 40%) was obtained as a light yellow solid. Rf=0.55 (Hexane/ethyl acetate 1:1); HRMS (ESI) (m/z) [MH]$^+$ called for $C_{18}H_{12}Cl_2N_3O_5S_3$, 513.9160, found 513.9179.

Synthesis of 5-[(3,5-dichloropyridin-4-yl)sulfanyl]-N-{3-[2-(dimethylamino)ethylamino]-1,1-dioxo-2,3-dihydro-benzothiophen-6-yl}-4-nitrothiophene-2-carboxamide (compound 20)

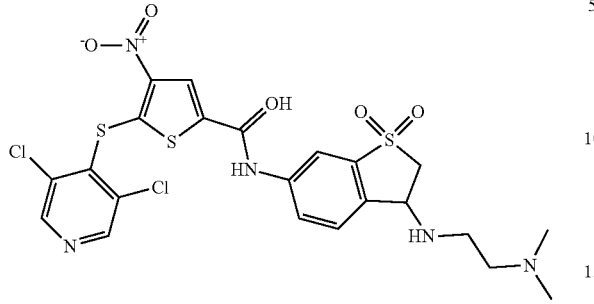

Compound 15 (50mg) was dissolved in (2-aminoethyl)dimethylamine (0.5 mL) and the reaction mixture was stirred at RT for 4 h. The residue was purified by preparative reverse phase HPLC using a linear gradient of 10-95% $CH_3CN$ over 15 min with a flow rate of 20 mL/min. After lyophilization, pure product (38 mg, 65%) was obtained as a light yellow solid. Rf=0.06 ($CH_2Cl_2$/MeOH 20:1); HRMS (ESI) (m/z) [MH]$^+$ calcd for $C_{22}H_{22}Cl_2N_5O_5S_3$, 602.0160, found 602.8691.

Synthesis of 5-[(3,5-dichloropyridin-4-yl)sulfanyl]-N-(1,1-dioxo-2,3-dihydro-benzothiophen-6-yl)-4-nitrothiophene-2-carboxamide (compound 16).

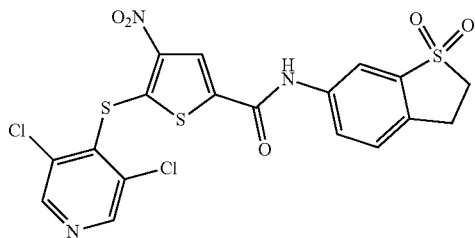 [SMILES: O=C(Nc1ccc2c(c1)S(=O)(=O)CC2)c1cc([N+](=O)[O-])c(Sc2c(Cl)cncc2Cl)s1]

Using the method for compound 15, 5-[(3,5-Dichloro-4-pyridinyl)sulfanyl]-4-nitrothiophene-2-carboxylic acid and Benzo[b]thiophen-6-amine, 2,3-dihydro-, 1,1-dioxide gave 5-[(3,5-dichloropyridin-4-yl)sulfanyl]-N-(1,1-dioxo-2,3-dihydro-benzothiophen-6-yl)-4-nitrothiophene-2-carboxamide (65% yield). Rf=0.27 (Hexane/acetone 2:1); HRMS (ESI) (m/z) [MH]$^+$ calcd for $C_{18}H_{12}Cl_2N_3O_5S_3$, 515.9316, found 515.9337.

Example 4

Synthesis of the Exemplary Iminosulfoxide, 5-[(3,5-dichloropyridin-4-yl)sulfanyl]-N-{3-[imino(methyl)oxo-sulfanyl]phenyl}-4-nitrothiophene-2-carboxamide (compound 22)

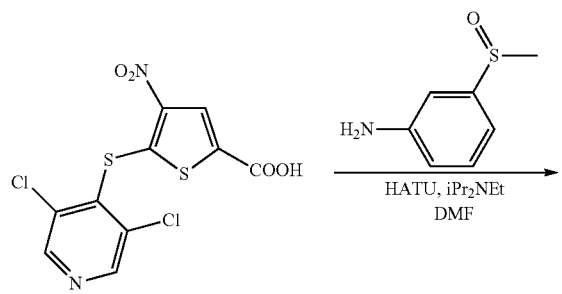

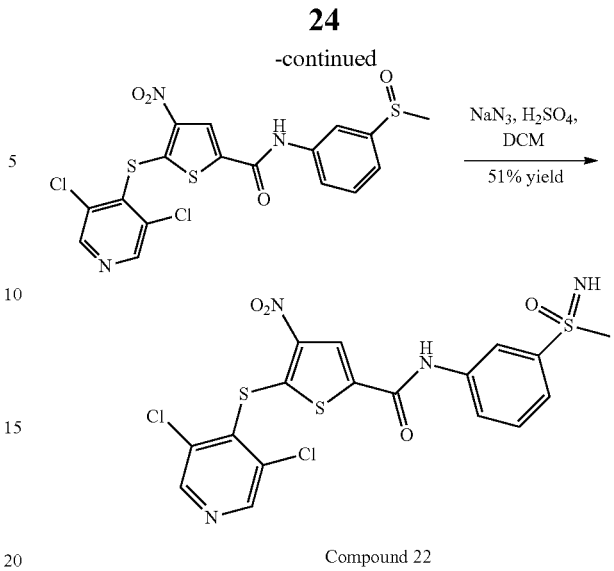

Compound 22

Using the method for compound 15, 5-[(3,5-Dichloro-4-pyridinyl)sulfanyl]-4-nitrothiophene-2-carboxylic acid and 3-methanesulfinylaniline gave 5-[(3,5-dichloropyridin-4-yl)sulfanyl]-N-(3-methanesulfinylphenyl)-4-nitrothiophene-2-carboxamide.

5-[(3,5-dichloropyridin-4-yl)sulfanyl]-N-(3-methanesulfinylphenyl)-4-nitrothiophene-2-carboxamide (30 mg, 0.06 mmol) in 2 mL DCM is treated with $NaN_3$ (5 mg, 0.072 mmol, 1.2 equiv). The mixture was slowly treated with 0.2 mL of concentrated $H_2SO_4$ at 0° C. and then slowly heated to 55° C. After 16 h, the reaction mixture was cooled to RT. The yellow solid precipitated and was washed with DCM. The residue was purified by preparative reverse phase HPLC using a linear gradient of 10-95% $CH_3CN$ over 15 min with a flow rate of 20 mL/min. After lyophilization, pure product (15 mg, 51%) was obtained as a light yellow solid.

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of excludes any element, step or material other than those specified in the claim and, in the latter instance, impurities ordinary associated with the specified material(s). The term "consisting essentially of limits the scope of a claim to the specified elements, steps or material(s) and those that do not materially affect the basic and novel characteristic(s) of the claimed invention. All compounds, compositions, and methods described herein that embody the present invention can, in alternate embodiments, be more specifically defined by any of the transitional terms "comprising," "consisting essentially of," and "consisting of."

REFERENCES

1. Cancer Facts and Figures, in American Cancer Society. 2011.
2. Swinder Singh, R. C. P., Thomas A. Baillie and Adrian Whitt, *The resurgence of covalent drugs*. Nature Reviews Drug Discovery, 2011. 10: p. 307-316.
3. Cao, P., J. Weinstock, W. D. Kingsbury, C. A. Leach, S. K. Kizhakkethil George, and B. Nicholson, *Antineoplastic compounds, compositions and methods*.
4. Nicholson, B. and K. G. Suresh Kumar, *The multifaceted roles of USP7: new therapeutic opportunities*. Cell Biochem Biophys, 2011. 60(1-2): p. 61-8.
5. Felle, M., et al., *The USP7/Dnmt1 complex stimulates the DNA methylation activity of Dnmt1 and regulates the stability of UHRF1*. Nucleic Acids Res, 2011. 39(19): p. 8355-65.
6. Qin, W., H. Leonhardt, and F. Spada, *Usp7 and Uhrf1 control ubiquitination and stability of the maintenance DNA methyltransferase Dnmt1*. J Cell Biochem, 2011. 112(2): p. 439-44.
7. Pedroza-Pacheco, I., A. Madrigal, and A. Saudemont, *Interaction between natural killer cells and regulatory T cells: perspectives for immunotherapy*. Cell Mol Immunol, 2013. 10(3): p. 222-9.
8. Wang, P. and S. G. Zheng, *Regulatory T cells and B cells: implication on autoimmune diseases*. Int J Clin Exp Pathol, 2013. 6(12): p. 2668-74.
9. Pardoll, D., *The blockade of immune checkpoints in cancer immunotherapy*. Nature Reviews Cancer, 2012. 12: p. 252-64.
10. Fridman W H, P. F., Sautes-Fridman C, Galon J, *The immune contexture in human tumours: impact on clinical outcome*. Nature Reviews Cancer, 2012. 12(298-306).
11. Wolchok, J. D., et al., *Nivolumab plus ipilimumab in advanced melanoma*. N Engl J Med, 2013. 369(2): p. 122-33.
12. d'Hennezel, E., et al., *FOXP3 forkhead domain mutation and regulatory T cells in the IPEX syndrome*. N Engl J Med, 2009. 361(17): p. 1710-3.
13. Bacchetta, R., F. Barzaghi, and M. G. Roncarolo, *From IPEX syndrome to FOXP3 mutation: a lesson on immune dysregulation*. Ann N Y Acad Sci, 2016.
14. Wang, L., et al., *Foxp3+ T-regulatory cells require DNA methyltransferase 1 expression to prevent development of lethal autoimmunity*. Blood, 2013. 121(18): p. 3631-9.
15. Obata, Y., et al., *The epigenetic regulator Uhrf1 facilitates the proliferation and maturation of colonic regulatory T cells*. Nat Immunol, 2014. 15(6): p. 571-9.
16. van Loosdregt, J., et al., *Stabilization of the transcription factor Foxp3 by the deubiquitinase USP7 increases Treg-cell-suppressive capacity*. Immunity, 2013. 39(2): p. 259-71.
17. Weinstock, J., et al., *Selective Dual Inhibitors of the Cancer-Related Deubiquitylating Proteases USP7 and USP47*. ACS Med Chem Lett, 2012. 3(10): p. 789-92.
18. Aitziber A. Sagardoy, M. J. G., Raquel Villar, María J. Viñas, Aranzazu Arrazola, Ignacio Encío, Victor Martinez-Merino, *Benzo[b]thiophene-6-carboxamide 1,1-dioxides:Inhibitors of human cancer cell growth at nanomolar concentrations*. Bioorg. Med. Chem., 2010. 18: p. 5701-5707.

What is claimed is:

1. A compound of formula (IV), including pharmaceutically acceptable salts, solvates and stereoisomeric forms thereof:

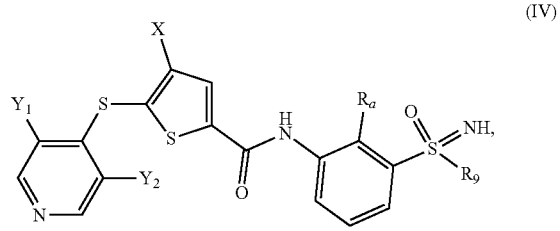

(IV)

wherein X is nitro or cyano;
$Y_1$ and $Y_2$ may be the same or different and represent halogen, alkyl or haloalkyl; and
$R_9$ is selected from the group consisting of optionally substituted alkyl, cycloalkyl, heterocycle, heteroaryl, heteroarylalkyl, alkoxy, and aryloxy; $R_a$ may be hydrogen, optionally substituted alkyl or optionally substituted cycloalkyl.

2. The compound of claim 1, wherein $R_9$ is a substituent selected from the group consisting of: methyl, ethyl, propyl, isopropyl, cyclopentyl, cyclopropyl, cyclopropyl methyl and trifluoromethyl.

3. A compound of formula (V), including pharmaceutically acceptable salts, solvates and stereoisomic forms thereof:

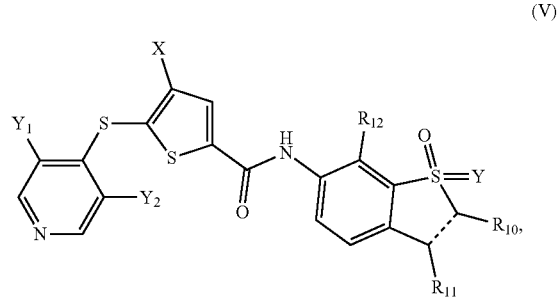

(V)

wherein X is nitro or cyano;
$Y_1$ and $Y_2$ may be the same or different and represent halogen, alkyl or haloalkyl; and
$R_{10}$ and $R_{11}$ may be independently selected from the group consisting of H, halo, hydroxyl, and optionally substituted alkyl, aryl, alkoxy, aryloxy, heteroaryl, cycloalkyl, heteroarylalkyl, amino, alkoxyalkylamino, monoalkylamino, dialkylamino and dialkylaminoalkylamino; $R_{12}$ may be hydrogen, optionally substituted alkyl or optionally substituted cycloalkyl; the dotted line represents a single bond or a double bond; and Y represents O or NH.

4. The compound of claim 3, wherein the compound is selected from the group consisting of:

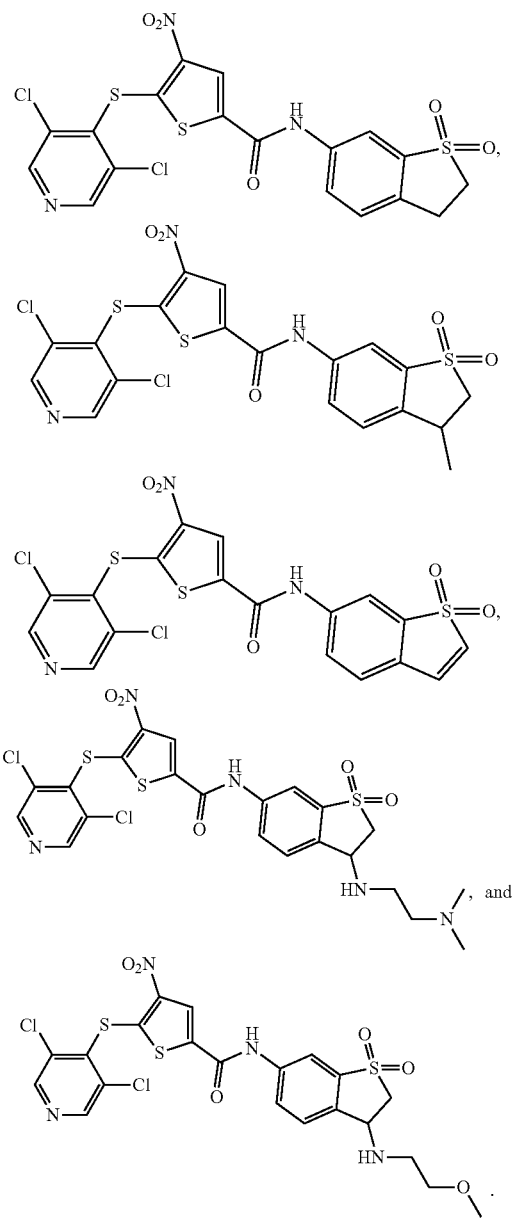

5. A pharmaceutical composition comprising at least one compound of claim 1,
and at least one of a physiologically acceptable carrier, diluent and excipient.

6. The pharmaceutical composition of claim 5, wherein $R_9$ is a substituent selected from the group consisting of: methyl, ethyl, propyl, isopropyl, cyclopentyl, cyclopropyl, cyclopropyl methyl, and trifluoromethyl.

7. A pharmaceutical composition comprising at least one compound of claim 3
and at least one of a physiologically acceptable carrier, diluent and excipient.

8. The pharmaceutical composition of claim 7, wherein the at least one compound is selected from the group consisting of:

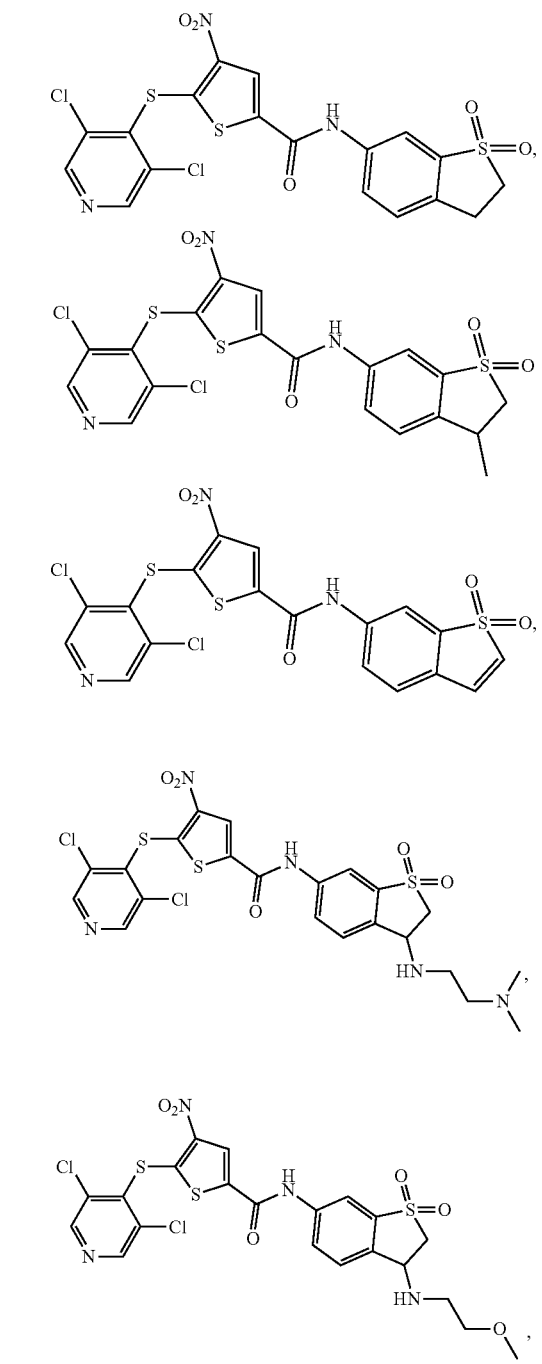

or the pharmaceutically acceptable salts, solvates and stereoisomeric forms thereof.

9. The pharmaceutical composition of claim 5, wherein the at least one compound comprises a solvate, a prodrug, or a combination thereof.

10. A compound of formula (VI), including pharmaceutically acceptable salts, solvates and stereoisomeric forms thereof:

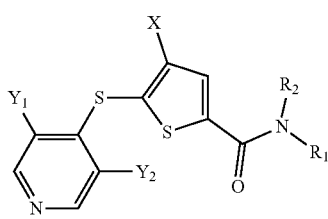

wherein X is nitro or cyano;
Y$_1$ and Y$_2$ may be the same or different and represent halogen, alkyl or haloalkyl;
R$_1$ represents an optionally substituted 1,1-dioxidotetrahydro-2H-thiopyran-4-yl group, which may be fused to an optionally substituted aryl, cycloalkyl, heteroaryl or heterocyclic group; and R$_2$ represents hydrogen or optionally substituted alkyl.

11. A pharmaceutical composition comprising at least one compound of claim 10 and at least one of a physiologically acceptable carrier, diluent and excipient.

12. The pharmaceutical composition of claim 11, wherein the at least one compound comprises a solvate, a prodrug, or a combination thereof.

13. The compound of claim 1, wherein X in said formula represents a nitro substituent; and Y$_1$ and Y$_2$ each represent a chloro substituent.

14. The pharmaceutical composition of claim 5, wherein X in said formula represents a nitro substituent, and Y$_1$ and Y$_2$ each represent a chloro substituent.

15. The compound of claim 1, wherein X in said formula represents a nitro substituent, and Y$_1$ and Y$_2$ each represent a fluoro substituent.

16. The pharmaceutical composition of claim 5, wherein X in said formula represents a nitro substituent; and Y$_1$ and Y$_2$ each represent a fluoro substituent.

17. The compound of claim 3, wherein R$_{12}$ in said formula represents a substituent selected from the group consisting of methyl, ethyl, propyl, isopropyl, cyclopentyl, cyclopropyl, cyclopropylmethyl, and trifluoromethyl.

18. The compound of claim 3, wherein X in formula V represents a nitro substituent, Y$_1$ and Y$_2$ each represent a chloro substituent and R$_{12}$ represents H.

19. The pharmaceutical composition of claim 7, wherein the at least one compound comprises a solvate, a prodrug, or a combination thereof.

20. The compound of claim 3, wherein X in said formula represents a nitro substituent; and Y$_1$ and Y$_2$ each represent a chloro substituent.

21. The pharmaceutical composition of claim 7, wherein X in said formula represents a nitro substituent, and Y$_1$ and Y$_2$ each represent a chloro substituent.

22. The compound of claim 3, wherein X in said formula represents a nitro substituent, and Y$_1$ and Y$_2$ each represent a fluoro substituent.

23. The pharmaceutical composition of claim 7, wherein X in said formula represents a nitro substituent; and Y$_1$ and Y$_2$ each represent a fluoro substituent.

24. The compound of claim 10, wherein X in said formula represents a nitro substituent; and Y$_1$ and Y$_2$ each represent a chloro substituent.

25. The pharmaceutical composition of claim 11, wherein X in said formula represents a nitro substituent, and Y$_1$ and Y$_2$ each represent a chloro substituent.

26. The compound of claim 10, wherein X in said formula represents a nitro substituent, and Y$_1$ and Y$_2$ each represent a fluoro substituent.

27. The pharmaceutical composition of claim 11, wherein X in said formula represents a nitro substituent; and Y$_1$ and Y$_2$ each represent a fluoro substituent.

* * * * *